United States Patent [19]

Mathiowitz et al.

[11] Patent Number: 5,718,921
[45] Date of Patent: Feb. 17, 1998

[54] MICROSPHERES COMPRISING POLYMER AND DRUG DISPERSED THERE WITHIN

[75] Inventors: Edith Mathiowitz, Brookline; Claudy J.P. Mullon, Cambridge; Abraham J. Domb, Brookline; Robert S. Langer, Somerville, all of Mass.

[73] Assignee: Massachusetts Institute of Technology, Cambridge, Mass.

[21] Appl. No.: 691,874

[22] Filed: Aug. 2, 1996

Related U.S. Application Data

[63] Continuation of Ser. No. 304,702, Feb. 1, 1989, abandoned, which is a continuation of Ser. No. 25,409, Mar. 13, 1987, abandoned.

[51] Int. Cl.$^6$ .................. A61K 9/50; A61K 9/52; B01J 13/12
[52] U.S. Cl. .................. 424/497; 424/425; 424/486; 427/2.21; 427/213.31; 427/213.36; 514/866; 514/963; 514/965
[58] Field of Search .................. 427/2.21, 213.31, 427/213.36; 424/486, 497; 514/866, 963, 965

[56] References Cited

U.S. PATENT DOCUMENTS

| | | | |
|---|---|---|---|
| 4,479,911 | 10/1984 | Fong | 264/4.6 |
| 4,585,651 | 4/1986 | Beck et al. | 514/963 X |
| 4,637,905 | 1/1987 | Gardner | 264/4.3 |
| 4,792,598 | 12/1988 | Ziegast | 528/206 |
| 4,906,474 | 3/1990 | Langer et al. | 424/497 X |

*Primary Examiner*—Richard K. Lovering
*Attorney, Agent, or Firm*—Arnall Golden & Gregory, LLP

[57] ABSTRACT

A method for preparation of biodegradable polymeric drug delivery devices using relatively low temperatures and non-aqueous solutions which is particularly useful with polyanhydrides, thermolabile drugs, and in forming multi-layered devices.

In a first embodiment, the polymer is dissolved in a volatile organic solvent, the drug is dispersed or dissolved in the polymer solution, the mixture is suspended in an organic oil, and the organic solvent is extracted into the oil, creating microspheres. The preferred polymers are polyanhydrides since they are biodegradable and have been proven to be useful in vivo.

In a second embodiment, the polymer is dissolved in organic solvent with or without the drug, and the mixture is suspended in glycerol. The suspension is frozen and the organic solvent slowly evaporated.

Using these embodiments, alone or in combination with other methods including the "hot melt" technique, multi-walled microspheres having each wall degrading at a different rate or containing different drugs can be manufactured.

8 Claims, 4 Drawing Sheets

MICROSPHERES COMPRISING POLYMER AND DRUG DISPERSED THERE WITHIN

BACKGROUND OF THE INVENTION

This is a request for filing a Continuation application under 37 C.F.R. §1.60 of prior application Ser. No. 07/304,702, filed on Feb. 1, 1989, and now abandoned, by Edith Mathiowitz, Claudy J. P. Mullon, Abraham J. Domb and Robert S. Langer for "Preparation of Polyanhydride Microspheres and Use in Controlled Drug Delivery," now abandoned, which is a continuation of U.S. Ser. No. 07/025,409 filed on Mar. 13, 1987, now abandoned.

The United States Government has rights in this invention by virtue of National Institute of Health grant numbers NIH-5-R01-GM 26698.

The present invention are new methods for preparing bioerodible polyanhydride microspheres, particularly for use in controlled drug delivery.

Biodegradable microspheres possess two important advantages in controlled drug delivery: they are injectable and they can be used for continuous release over an extended period of time.

The preferred polymers for making biodegradable drug delivery devices are polyanhydrides. These have been demonstrated to degrade into non-toxic small molecules that are non-mutagenic, non-cytogenic, and non-teratogenic; they are highly biocompatible and non-inflammatory; the release rates can be altered over a thousand fold by simple changes in the polymer backbone; and very hydrophobic polyanhydrides have been shown to display surface erosion.

Previous work with polyanhydride microspheres has utilized a hot-melt technique to show the possibility of incorporating macromolecules, including drugs, into devices formed of bioerodible polyanhydrides. In the hot-melt technique, the melted polymer is mixed with the drug and the mixture is suspended in a non-solvent and cooled down. The advantages of the system are many: the capsules are obtained in high yields as free flowing powder, they display surface erosion depending on the amount of drug used and they are suitable to all kinds of drugs, even hydrophilic ones since the process is carried on in organic solvents. The big disadvantage of these microspheres is the fact that only low melting point polymers can be used, since otherwise the drugs may lose their biological activity due to high temperatures.

An alternative method is the solvent evaporation or phase separation technique. The preparation of microspheres by evaporation of organic solvent from an emulsion has been disclosed by, for example, U.S. Pat. No. 3,523,906 to M. N. Vrancken and U.S. Pat. No. 3,960,757 to M. Morishita. These processes have been used extensively to prepare microspheres from biodegradable polymers, as reported in the literature and by H. Jaffe in U.S. Pat. No. 4,272,398. The procedure consists of dissolving the polymer in methylene chloride or another volatile solvent, dissolving or suspending the drug in the polymer solution and emulsifying the resulting mixture in an aqueous phase containing an emulsifier. The solvent is allowed to evaporate. The result is drug-loaded microspheres. In another variation of this method described by L. M. Sanders in *J. Pharm. Science* 73(9), 1294–1297 (Sept. 1984) polylactic acid microspheres are formed by suspension of the polymer in an aqueous solution. The primary disadvantage of this method with respect to polyanhydrides is the use of aqueous solutions which initiates polymer hydrolysis.

Polyanhydrides possess a water labile linkage and a hydrophobic backbone. The anhydride bond is hydrolytically more active than the amide, ester or ether bond of polymers such as polylactide and polylactide copolymers. Even the aromatic polyanhydrides which are more stable hydrolytically are still sensitive to traces of water. Although this property provides the basis for using a variety of backbones and ensures biodegradability, the labile bond prevents the use of frequently employed methods of microencapsulation such as those described above.

It is therefore an object of the present invention to provide a method for manufacturing polymeric devices for drug delivery wherein the polymer is dissolved in a non-aqueous organic solvent.

It is a further object of the present invention to provide a method for manufacturing polymeric devices using hydrophobic polymers.

It is another object of the present invention to provide a method for making polymeric drug delivery devices at relatively low temperatures, thereby preserving biological activity of the drug to be delivered.

It is yet another object of the present invention to provide a method for producing multi-layer devices formed from different types of polymers.

SUMMARY OF THE INVENTION

A method for preparation of polymeric drug delivery devices using relatively low temperatures and non-aqueous solutions which is particularly useful with polyanhydrides, biological or labile drugs, and in forming multi-layered devices.

In a first embodiment, the polymer is dissolved in a volatile organic solvent, the drug is dispersed or dissolved in the polymer solution, the mixture is suspended in an organic oil, and the organic solvent is extracted into the oil, creating microspheres.

The method enables the preparation of microspheres from a variety of biodegradable polymers, including hydrophobic polyanhydrides such as (pCPP:SA, 50:50) and CPP copolymerized with dodecanedoic acid (DD), (pCPP:DD, 20:80) and (pCPP:DD, 50:50). The preferred polymers are polyanhydrides although polyorthoesters and polylactic acid polymers and copolymers may be used by judiciously selecting the polymers, organic solvent and organic oil to result in the same or similar solubility and precipitation of the polymer in the organic oil as is demonstrated by the following examples utilizing polyanhyrides.

In a second embodiment, the polymer is dissolved in organic solvent with or without the drug, and the mixture is suspended in glycerol. The suspension is frozen and the organic solvent slowly evaporated. After two days, the microspheres are washed with ethanol.

Using these embodiments, alone or in combination with other methods known to those skilled in the art including the "hot melt" technique, multi-walled microspheres having each wall degrading at different rates can be manufactured. This can be achieved by applying different coatings, each one being a different type of polymer, where the inner core is the most hydrophilic and the outer ones are less so. The rational is to compensate for the loss of surface area by using slower degrading polymers. In this case one can achieve both surface erosion and zero order release with microspheres.

In the given examples, multi-wall microspheres were prepared as follows: the first core was prepared by the solvent removal method of the present invention. The second layer was applied using the hot-melt technique. The polymer used for the first layer was (p-carboxyphenoxy) propane copolymerized with sebacic acid (1:1)(melting point 147° C.). The pCPP:SA microspheres were then suspended in pCPP:SA (1:4) polymer (melting point 74° C.). The mixture was suspended in silicon oil and cooled down to room temperature. This kind of process can be repeated as long as the inner core has a higher melting point than the layer being applied.

DETAILED DESCRIPTION OF THE PRESENT INVENTION

Figure 1:
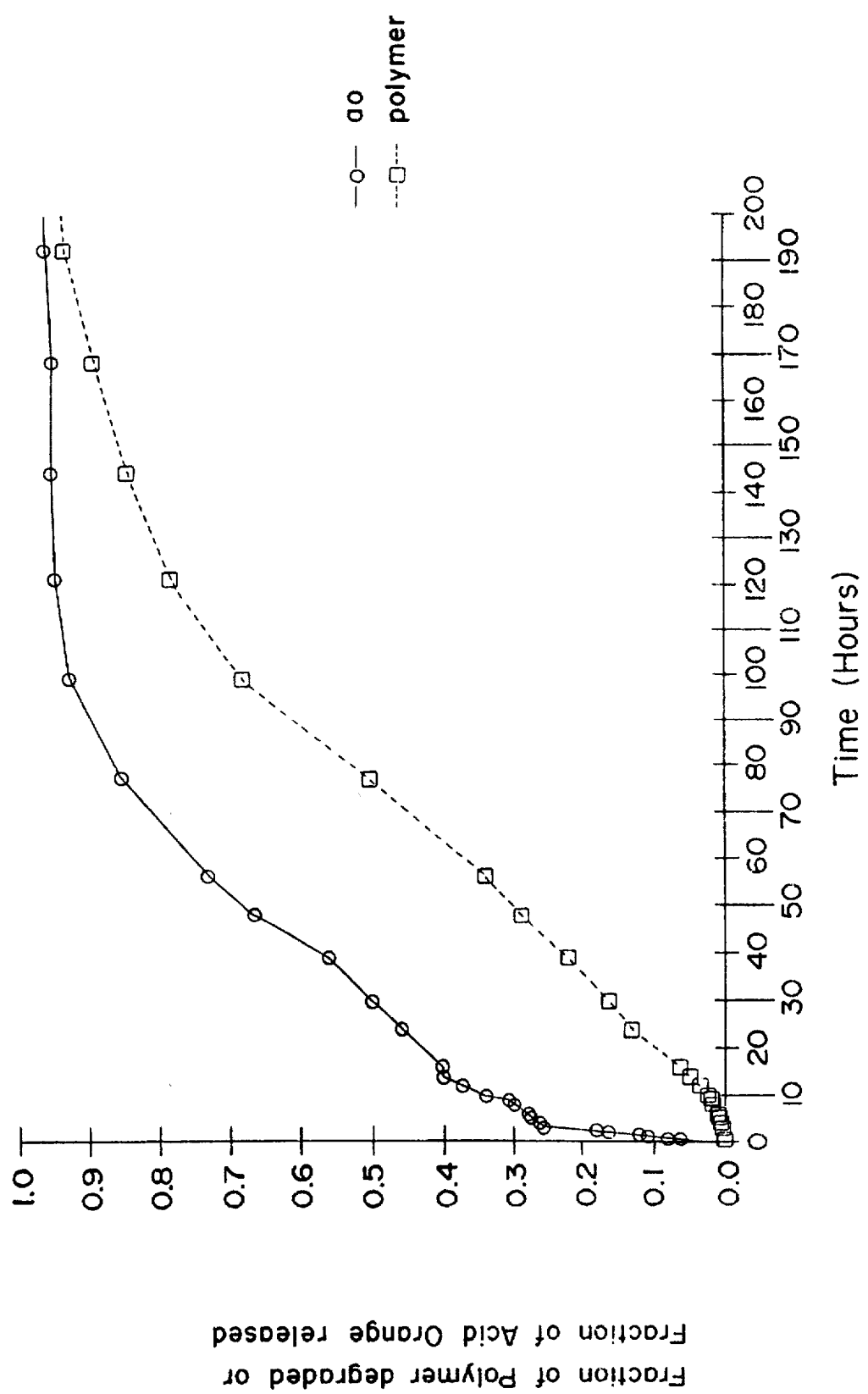
FIG. 1 is a graph of the polymer erosion of and percent-release of acid orange from 600–700 micron pCPP:SA, 20:80 microspheres made according to the method of the present invention, as a function of time (hours).

The present invention is the manufacture of controlled drug delivery devices from biodegradable polymers using methods resulting in the formation of microspheres incorporating the drug to be released, wherein the temperature of formation is low enough not to destroy biological activity of the drug and non-aqueous solutions are used to avoid adverse effects on the polymers.

In the preferred embodiment, polyanhydrides are selected for their degradation properties, melting point, and molecular weight, as well as solubility and precipitation properties in the inert viscous solution, either glycerol or an organic oil such as silicon oil, vegetable oils, paraffin, and mineral oil. However, it has been demonstrated that similar results can be obtained with other biodegradable polymers such as polyorthoesters and polymers and copolymers of lactic acid using a judicious selection of the polymer, solvent, and organic oil.

Using one embodiment of the method of the present invention, low molecular weight polyanhydride microspheres are prepared as follows:

One gram of a selected polymer, for example, pCPP:SA, 20:80, mw=16000, is dissolved in 5 ml methylene chloride, the drug or dye to be released from the polymer suspended in the polymer solution, and the mixture dropped into silicon oil (Dow Chemical Company, Midland, Mich.) that contains between approximately 1.0 and 20% of Span™ or another surfactant or emulsifying agent. Span™ emulsifiers are preferred. This is then stirred at a set stirring rate. Stirring was done using an overhead stirrer type RZR50, ("CAFRAMA", Wiarton, Ont.) and a three-blade impeller. After 1 hour, petroleum ether is introduced and stirring is continued for another hour. The microspheres are isolated by filtration, washed with petroleum ether, dried overnight in a lyophilizer (Labconco, Freeze Dryer 8), sieved (U.S. Standard Sieve Series, Newark, Wire Cloth Company, Newark, N.J.) and stored at less than 0° C.

The key element to the success of the method is the dissolution of the polymer is a non-aqueous solvent and extraction of the solvent into the organic oil.

This embodiment of the method yields microspheres with diameters of from 50 to 1000 microns. The recovery in the example was 40% due to some polymer precipitating on the stirrer.

Although this embodiment works well enough with low molecular weight polymers such as pCPP:SA, 20:80, mw 16,000, the process results in rods rather than microspheres when applied to polymers of higher molecular weight and higher percentage of CPP.

Accordingly, a variation of this embodiment is used to prepare higher molecular weight polyanhydride microspheres. Two grams polymer is dissolved in 10 ml of methylene chloride, the drug added and the mixture suspended in silicon oil containing Span 85 (0%–20%) and a known amount of methylene chloride. The amount depends on the type of polymer used and its molecular weight. For example, for pCPP:SA, 20:80, with molecular weight of 30,000–40,000, the ratio between the silicon oil and the methylene chloride is 5:1 and for pCPP:SA, 50:50, mw 40,0000, the ratio is 1:1. The optimum ratio can be determined empirically by one skilled in the art. The drug particle size is preferably less than 50 microns. After dropping the polymer solution into the silicon oil, a non-solvent such as petroleum ether is added to increase the rate of precipitation and the stirring continued for two hours, or as necessary. In general, the amount of non-solvent is determined by the rate of precipitation, increasing the amount of solvent to increase the rate of precipitation. The rate of precipitation can be decreased by slowing the rate at which polymer is added to the organic oil. The microspheres are then isolated by filtration, washed with petroleum ether, dried overnight in a lyophilizer and stored in less than 0° C.

This variation of the method produces microspheres ranging from 10 to 300 microns in diameter. The yield is more than 85% and almost no precipitation on the stirrer is observed. The process is reproducible to within 5% with respect to yield and size distribution when polymer with the same molecular weights are used.

The primary elements in this variation is the dilution of the organic oil prior to dropping in the polymer solution using the polymer solvent and the use of the non-solvent to control the rate of precipitation of the polymer-drug mixture.

In the second embodiment of the method of preparation of microsphere according to the present invention, the polymer is dissolved in organic solvent, simultaneously with or before addition of the drug, and the mixture is suspended in glycerol. The suspension is frozen and the organic solvent evaporates slowly. After two days, the microspheres are washed with ethanol.

Multi-wall microspheres are prepared using the method of the present invention as follows: the first core is prepared by either of the solvent removal methods. The second layer is preferably applied by a different method such as the hot melt method, described in the Background of the Invention, being careful to select the second polymer to have a lower melting point than the first polymer.

In an example of this method, a first polymer layer was constructed of (p-carboxyphenoxy) propane copolymerized with sebacic acid (pCPP:SA, 1:1) (melting point 147° C.). A second layer was applied by suspending the pCPP:SA, 1:1, microspheres in melted pCPP:SA, 1:4, polymer (melting point 74° C.). The mixture was then suspended in silicon oil and cooled down to room temperature.

This kind of process can be repeated for as long as the inner core has the higher melting point. The outing coatings can also be applied by methods known to those skilled in the art such as by fluidized-bed, spraying, etc.

The controlled release of drugs made according to the method of the present invention is demonstrated by the following non-limiting drug release studies:

All drugs used are sieved to a size less than 50 microns in diameter for loading into the microspheres. A dye, p-nitro aniline or acid orange, which is soluble in methylene chloride, is used to measure drug release in the following examples of the methods and products of the present invention. Insulin is used as an example of a biologically active molecule for release both in vitro and in vivo. Insulin was selected since the development of an injectable erodible system for insulin is still a challenge and is the subject of many investigations.

The polymer used in the examples of drug delivery systems is pCPP:SA, 1:1.

Drug loading is measured for the dyes by the cumulative release. For insulin loading, the microspheres are dissolved in methylene chloride and the insulin extracted by water. 95% of the insulin was retained by the microspheres for both loadings that were used (5% and 10% insulin).

The insulin loading eluents are passed through a Perkin Elmer HPLC system containing a reversed phase Vydac peptide/protein $C_{18}$ column (Rainin) to identify the insulin. A segmental gradient of acetonitrile (EM Science) (20% to 80% acetonitrile) and glass-distilled water (EM Science) with 3% trifluoroacetic acid (EM Science) for 20 min is used. Insulin is detected at 220 nm. No change in retention time is observed from insulin extracted from the microspheres as compared to free insulin (12.22 min). Molecular weights of the polymer microspheres measured immediately after preparation and after six months storage at −20° C. indicate no significant changes.

The surface morphology of microspheres are studied, after preparation and after degradation, via Stereomicroscopy and Scanning Electron Microscopy (SEM) (ISI Model DS-130). Cross-sections of samples are obtained by embedding the microspheres in mounting media (Histo Prep SO-H-75 Frozen Tissue Embedding Media, Fisher Scientific) and cutting 10 micron sections at less than 20° C. with a microtome (International Equipment Company, a division of DAMON). Samples for SEM are dried, mounted on metal stubs and sputter-coated with gold-palladium in a Polaron Instrument E5100.

Figure 2:
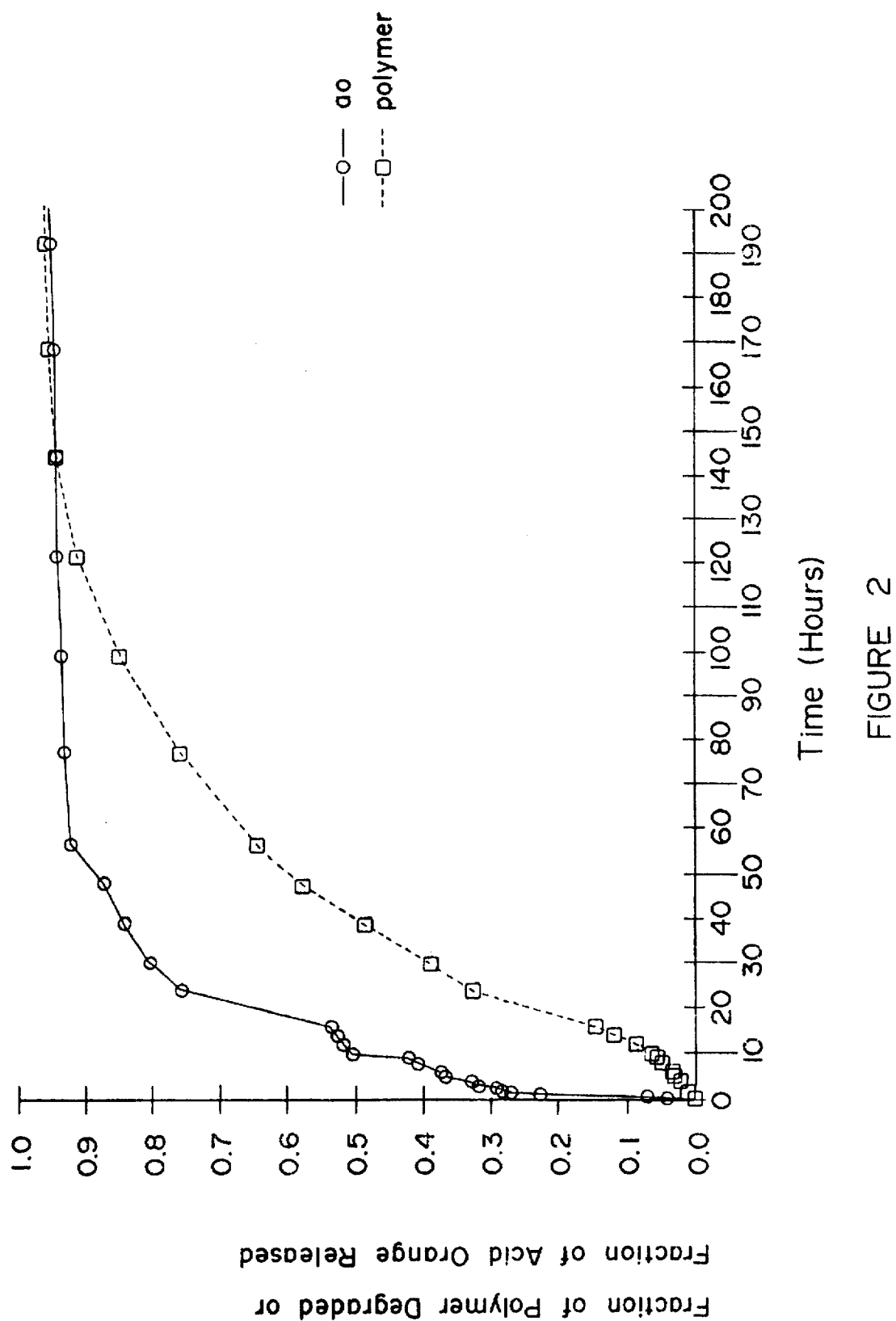
FIG. 2 is a graph of the polymer erosion of and percent release of acid orange from larger pCPP:SA,20:80 microspheres, greater than 1180 microns, made according to the method of the present invention, as a function of time (hours).

In vitro dye release from microspheres:

The microspheres and measurements were made as follows. The release of acid orange from pcPP:sA, 20:80, microspheres, formed by mixing the polymer and dye together and dropping into silicone oil is shown in FIGS. 1 and 2. FIG. 1 demonstrates the release over approximately one week for acid orange from microspheres with a diameter of 600–700 microns. The release is higher correlated with the degradation of the polymer and appears almost linear over time. The release from microspheres with diameters of 1180 microns is shown in FIG. 2. Again, the release is highly correlated with the degradation of the polymer, but is slightly more rapid than with the smaller diameter microspheres.

Dye or insulin-incorporated microspheres were sieved into different size ranges. Release experiments were conducted in 10 to 50 ml 0.1N pH 7.4 phosphate buffer at 37° C. in a small Bio-Rad polypropylene Econo-column, 10 ml, (Bio-Rad Laboratories). Gentamicin Sulphate (Sigma Chemical Co., St. Louis, Mo.) was used at a concentration of 0.05 mg/ml as an antibacterial agent. The buffer was changed every hour for the first day, then three times per day for several days, then once every two to three days. Each experiment was performed in duplicate with less than 3% error.

The polymer erosion and drug release kinetics were followed by measuring the UV absorption of the buffer solution with a Perkin Elmer UV spectro-photometer. Polymer degradation products were measured at 247 nm. Different dyes were measured at visible wave lengths: acid orange at 490 nm, p-nitroaniline at 380 nm. When drugs showed absorption in both the UV and visible regions, extinction coefficients were measured at appropriate wave lengths and the contribution to the UV absorption calculated and subtracted.

An in vitro protein assay was implemented to assess insulin release kinetics. This assay uses a protein reagent manufactured by Bio-Rad Laboratories. Because the Bio-Rad reagent has been shown to react with very high concentrations of the polymer degradation products, care is taken to dilute the eluent to a point where reaction of breakdown products with the Bio-Rad reagent is very low relative to the reaction of the reagent with insulin. A standard curve for the reaction of polymer breakdown products was also constructed. With the extinction coefficient obtained from this curve, it is possible to subtract a calculated absorbance due to the presence of breakdown product.

Figure 3A:
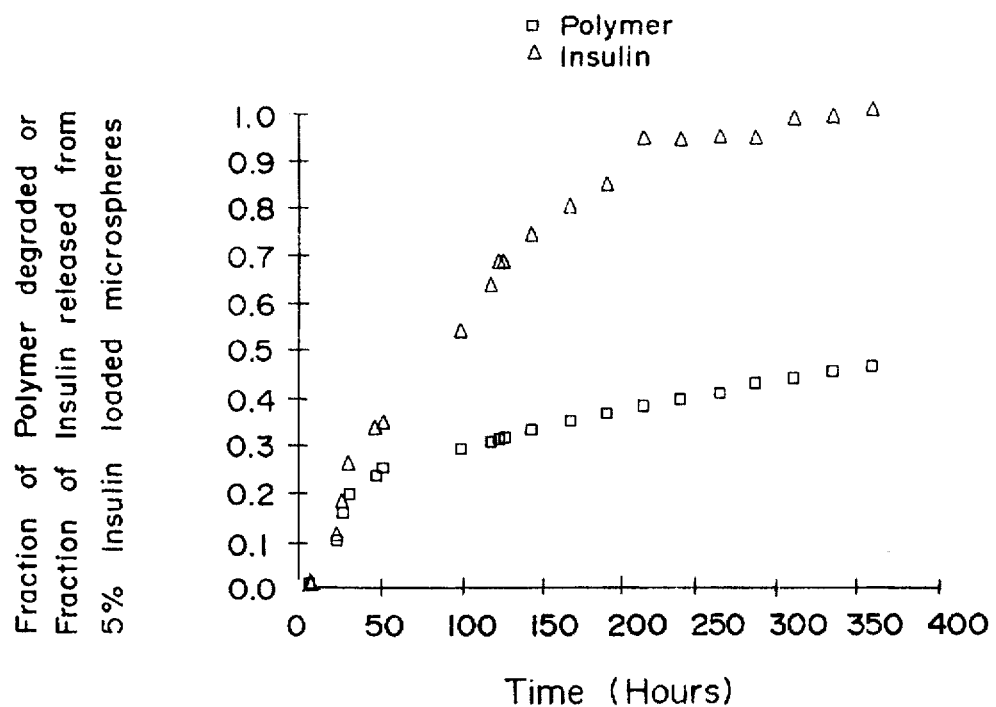
FIG. 3 are graphs of the polymer erosion and percent insulin release from pCPPA:SA, 50:50, microspheres made according to the present invention, over time (hours), as a function of percent loading, 5% loading (FIG. 3a) and 10% loading (FIG. 3b).
Figure 3B:
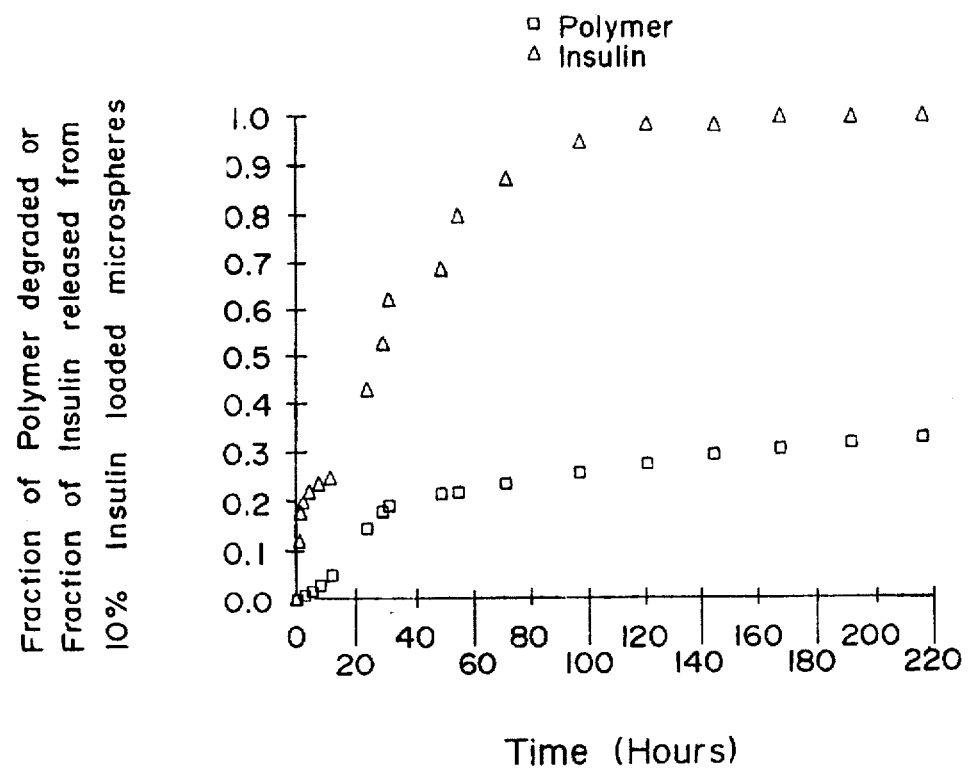

Insulin release in vitro from microspheres:

FIG. 3a is the in vitro release of insulin from pCPP:SA, 1:1, microspheres (0–300 microns, made by solvent removal with 5% insulin loading) correlated with the degradation of the polymer over time. FIG. 3b is the release and degradation of the same microspheres with 10% insulin loading.

These results demonstrate the linearity of the release of the insulin with degradation of the polymer.

Insulin release in vivo from microspheres:

Actual biological activity of insulin released from microspheres formed according to the method of the present invention was determined in vivo by monitoring daily blood and urine glucose levels in polymer-implanted diabetic female Sprague-Dawley rats. Diabetes was induced by injection into the tail vein of 65 mg/kg of streptozotocin (The Upjohn Company, Kalamazoo, Mich.) in 0.1M citrate buffer pH 4.5, the optimal dose for inducing diabetes in rats. An induction period of seven to ten days after streptozotocin injection is necessary to induce the clinical onset of diabetes mellitus.

When serum glucose levels reached a minimum of 400 mg/dl, rats were treated with the polyanhydridein-insulin microspheres. Initially, microspheres were suspended in physiologic saline and then injected subcutaneously through a standard 18 gauge needle. The best media for injection for suspending the microspheres is an oil. However, to avoid other factors that could influence the release, microspheres were implanted through a small (1 cm) surgical incision through the skin of the dorsum of the rat. Microspheres were places subcutaneously and the skin was closed with 5-0 Ethilon mono-filament nylon sutures (Ethicon, Inc.). Sterile techniques were employed during all phases of the surgical procedure. Rats were housed in metabolic cages and were fed ad libidum. Both healthy and diabetic control rats were housed concurrently with the treated rats. Daily urine glucose outputs were estimated with Chemstrips UG (Bio-Dynamics). Blood was drawn daily from the tail vein and serum glucose levels were read on a YSI Model 23A glucose Analyzer.

Figure 4A:
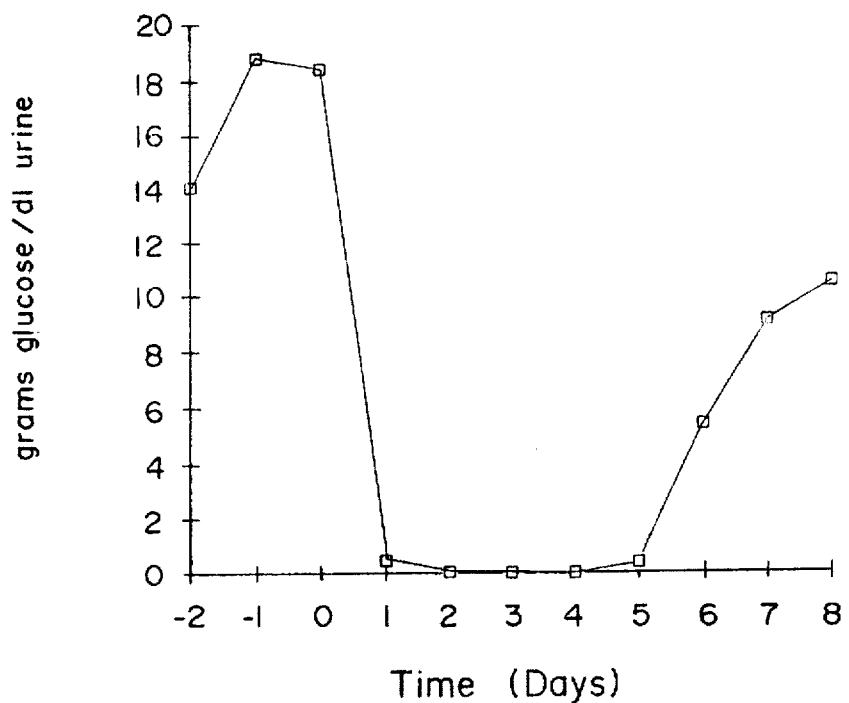
FIG. 4a is a graph of glucose in urine over time (days) in diabetic rats implanted with pCPP:SA, 50:50, microspheres with 10% insulin loading, made according to the present invention.
Figure 4B:
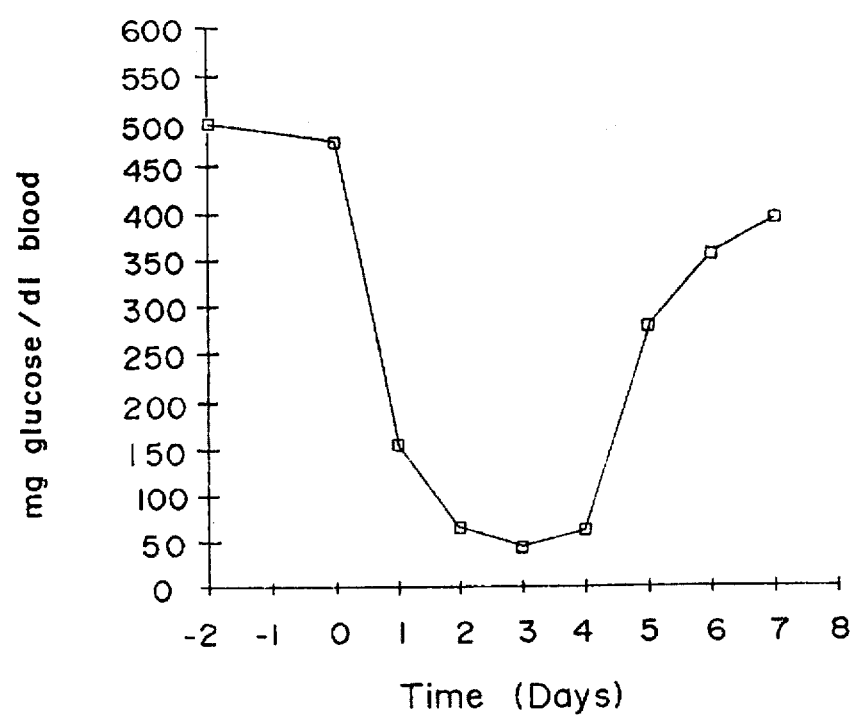
FIG. 4b is a graph of glucose blood over time (days) in diabetic rats implanted with pCPP:SA, 50:50, microspheres with 10% insulin loading, made according to the present invention.

The microspheres were the same as in the in vitro examples, pCPP:SA, 1:1, with 10% insulin loading. The results are shown in FIGS. 4a and 4b. As in the in vitro studies, the insulin release is initially linear, and the physiological response (a decrease in blood and urine glucose levels) is sustained over time in a uniform manner.

The polymeric devices produced according to the method of the present invention are especially useful in drug delivery, as shown by the preceding example of insulin release in vivo. The advantage of the method is that thermolabile drugs and biological molecules can be dispersed within the microspheres. The further advantage of the method is in the manufacture of multi-layered polymeric devices which can be used to deliver staggered release of one or more drugs, at the same or different release rates.

Variations and modifications of the method of the present invention, a process for making polymeric drug delivery devices at decreased temperatures, in the absense of water, having one or more layers of polymer, and the polymeric devices produced thereby, will be obvious to those skilled in the art from the foregoing detailed description. Such modifications and variations are intended to come within the scope of the appended claims.

We claim:

1. Microspheres comprising a polymer and a drug dispersed within each microsphere, whereby the microspheres are formed in the absence of water by extraction into an organic oil of a volatile organic solvent from a non-aqueous solution of the polymer and the drug in the volatile organic solvent, wherein the organic oil is selected from the group consisting of silicon oil, vegetable oil, paraffin, and mineral oil, the polymer is selected from the group of biodegradable polymers consisting of polyanhydrides, polyorthoesters, polylactic acid polymers, and combinations thereof, and the drug is a biological or labile drug.

2. The microspheres of claim 1 wherein the polyanhydride is selected from the group consisting of poly copolymerized with sebacic acid, poly copolymerized with dodecanedoic acid, and combinations thereof.

3. The microspheres of claim 1 wherein the polymer is a polyanhydride having a molecular weight of less than about 17,000.

4. The microspheres of claim 1 wherein the polymer is a polyanhydride having a molecule weight of greater than approximately 16,000 and the organic solvent is extracted into a mixture of the organic oil diluted with an organic solution.

5. The microspheres of claim 1, further comprising an additional polymer layer, wherein the additional polymer is applied to the surface of the microspheres by a hot melt technique and the additional polymer has a higher melting point than the polymer forming the microspheres of claim 1.

6. The microspheres of claim 5 wherein the polymer layers are formed of polyanhydrides having melting points less than the melting point of the polymer forming the underlying substrate.

7. The microspheres of claim 1 further comprising an additional polymer layer, and drug dispersed within or between the additional polymer layer.

8. The microspheres of claim 1 further comprising an additional polymer layer, wherein the outer layer is formed of a less hydrophilic polymer than the polymer forming the underlying microsphere.

* * * * *